United States Patent
Kim et al.

(12)

(10) Patent No.: US 12,186,356 B2
(45) Date of Patent: Jan. 7, 2025

(54) COMPOSITION FOR PREVENTING, ALLEVIATING, OR TREATING ALLERGIC SKIN DISEASE COMPRISING AS ACTIVE INGREDIENT EXTRACT OF GARDENIA FRUIT FROM WHICH PIGMENT IS REMOVED

(71) Applicant: KOREA INSTITUTE OF ORIENTAL MEDICINE, Daejeon (KR)

(72) Inventors: Ho Kyoung Kim, Daejeon (KR); Sun Haeng Park, Daejeon (KR); Seol Jang, Chungcheongnam-do (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 874 days.

(21) Appl. No.: 17/258,253

(22) PCT Filed: Jul. 10, 2019

(86) PCT No.: PCT/KR2019/008506
§ 371 (c)(1),
(2) Date: Jan. 6, 2021

(87) PCT Pub. No.: WO2020/013610
PCT Pub. Date: Jan. 16, 2020

(65) Prior Publication Data
US 2021/0268059 A1  Sep. 2, 2021

(30) Foreign Application Priority Data

Jul. 10, 2018 (KR) .................. 10-2018-0080056

(51) Int. Cl.
| | | |
|---|---|---|
| *A61K 36/744* | (2006.01) | |
| *A23L 5/20* | (2016.01) | |
| *A23L 33/00* | (2016.01) | |
| *A23L 33/105* | (2016.01) | |
| *A61P 17/04* | (2006.01) | |
| *A61P 37/08* | (2006.01) | |
| *B01D 11/02* | (2006.01) | |
| *B01D 15/12* | (2006.01) | |

(52) U.S. Cl.
CPC .............. *A61K 36/744* (2013.01); *A23L 5/23* (2016.08); *A23L 5/273* (2016.08); *A23L 33/105* (2016.08); *A23L 33/40* (2016.08); *A61P 17/04* (2018.01); *A61P 37/08* (2018.01); *B01D 11/0288* (2013.01); *B01D 15/125* (2013.01); *A23V 2002/00* (2013.01); *A61K 2236/331* (2013.01); *A61K 2236/333* (2013.01); *A61K 2236/39* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| | | | |
|---|---|---|---|
| KR | 10-2001-0096213 A | | 11/2001 |
| KR | 100543897 B1 | * | 1/2006 |
| KR | 20060089908 | * | 8/2006 |
| KR | 20100110046 | * | 10/2010 |
| KR | 10-1089637 B1 | | 12/2011 |
| KR | 10-1165716 B1 | | 7/2012 |
| KR | 10-2013-0121600 A | | 11/2013 |

OTHER PUBLICATIONS

Sung et al. (The Gardenia jasminoides extract and its constituent, geniposide, elicit anti-allergic effects on atopic dermatitis by inhibiting histamine in vitro and in vivo, Journal of Ethnopharmacology, 156(2014) 33-40). (Year: 2014).*
International Search Report for PCT/KR2019/008506 mailed on Oct. 7, 2019.
Sung Yoon-Young et al., "The Gardenia jasminoides extract and its constituent, geniposide, elicit anti-allergic effects on atopic dermatitis by inhibiting histamine in vitro and in vivo", Journal of Ethnopharmacology, vol. 156, pp. 33-40, 2014.
Trishna Debnath et al., "Anti-allergic and anti-atopic dermatitis effects of Gardenia Fructus extract", Food and Agricultural Immunology, vol. 29, No. 1, pp. 665-674, 2018.

* cited by examiner

*Primary Examiner* — Melissa S Mercier
(74) *Attorney, Agent, or Firm* — The PL Law Group, PLLC

(57) ABSTRACT

The present invention relates to a composition for preventing, alleviating, or treating allergic skin diseases comprising, as an active ingredient, an extract of *gardenia* fruit from which pigment is removed, and since the extract of *gardenia* fruit from which pigment is removed is more effective for allergic skin diseases compared to an extract of *gardenia* fruit from which pigment is not removed, the composition can be very advantageously used for allergic skin diseases, in particular, atopic dermatitis.

7 Claims, 5 Drawing Sheets

COMPOSITION FOR PREVENTING, ALLEVIATING, OR TREATING ALLERGIC SKIN DISEASE COMPRISING AS ACTIVE INGREDIENT EXTRACT OF GARDENIA FRUIT FROM WHICH PIGMENT IS REMOVED

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/008506, filed Jul. 10, 2019, which claims priority to the benefit of Korean Patent Application No. 10-2018-0080056 filed in the Korean Intellectual Property Office on Jul. 10, 2018, the entire contents of which are incorporated herein by reference.

TECHNICAL FIELD

The present invention relates to a composition for preventing, alleviating, or treating allergic skin diseases comprising, as an active ingredient, an extract of *gardenia* fruit from which pigment is removed.

BACKGROUND ART

An allergy is a hypersensitivity reaction of some people to a certain substance that typically does not exhibit any influence on normal people, in which the hypersensitivity reaction is caused by malfunction of an immune system to show skin hives, itch, runny nose, or cough. According to the World Health Organization (WHO), allergic diseases have been already included in the seven major diseases that can be the biggest problem in the $21^{st}$ century. As major allergic disease, there are atopy dermatitis, asthma, rhinitis, or the like. An allergy is a disease close to an incurable disease of modern medicine such that no established therapeutic agent exists at the present moment. Due to current use of antihistamines that are not a therapeutic agent per se for treating allergic disease and also steroids having many adverse effects in spite of excellent positive effects, the diseases are worsened and economic burden of patients is continuously increasing.

In general, atopy symptoms and an allergic disease occur in conjunction with an industrial progress, westernization of diets, higher preference for instant foods, an occurrence of severe environmental contamination, and a new kind of disease like sick building syndrome, and they tend to increase even more in the $21^{st}$ century. The incidence rate of allergic diseases is high not only in S. Korea and Western countries but also in developing countries that are under development. As such, it is expected that a therapeutic agent for the diseases would have a great demand across the world.

Atopic dermatitis is a chronic and recurrent inflammatory skin disease accompanied by severe itching (itchy feeling), eczematous skin disease, xeroderma, or the like, and it has been first identified by Wise and Sulzberger in the 1930s. Atopic dermatitis generally occurs during infancy or childhood, and, with recurrent moderate to severe symptoms, spontaneously disappears with age. However, sometimes the condition persists into adulthood. With regard to the patients suffering from atopic dermatitis in S. Korea, prevalence is 10 to 30% among children while it is 1 to 3% among adolescents. Atopic dermatitis is known to be a complex disease that is related with both the environmental factors and genetic factors. With regard to the factors influencing the occurrence rate of atopic dermatitis in recent years, it is believed that many factors are involved in complicated way including air pollution, nuclearization of the families, lower rate of breastfeeding, higher household income and higher education level, greater exposure to antigens due to frequent use of antibiotics, change in living environments, introduction of new antigens due to industrial progress, and the like.

Meanwhile, *gardenia* fruit is a fruit of *Gardenia jasminoides*, which is a plant belonging to Rubiaceae. *Gardenia* fruit is known to be useful as anti-inflammatory agent, diuretic agent, or hemostatic agent, or for treatment of jaundice. With use of an acid or an ash as a dye fixative, it is also used for dyeing textiles or pickled radish yellow, or dyeing Korean mung bean pancake, or fried fish or vegetable pancake yellow.

As a prior art related to *gardenia* fruit, a method of producing *gardenia* fruit extract with enhanced anti-inflammatory activity including treatment of *gardenia* fruit extract with β-glucosidase is described in Korean Patent Registration No. 1089637, and, in Korean Patent Registration No. 1165716, a composition for preventing or treating allergic disease comprising a fraction of *gardenia* fruit extract as an active ingredient is disclosed. However, so far there is no disclosure of a composition for preventing, alleviating, or treating allergic skin diseases comprising, as an active ingredient, an extract of *gardenia* fruit from which pigment is removed as it is disclosed in the present invention.

SUMMARY

The present invention is devised under the circumstances described above. The present invention provides a composition for preventing, alleviating, or treating allergic skin diseases comprising, as an active ingredient, an extract of *gardenia* fruit from which pigment is removed. Specifically, by finding that, according to the treatment with an extract of *gardenia* fruit from which pigment is removed, number of scratching decreases and the inflammatory cells and mast cells are reduced in an animal model with atopic dermatitis and, even when compared to an extract of *gardenia* fruit from which pigment is not removed, in particular, the number of scratching decreases and the inflammatory cells and mast cells are reduced, the present invention is completed.

To achieve the purpose described above, the present invention provides a pharmaceutical composition for preventing or treating allergic disease comprising, as an active ingredient, an extract of *gardenia* (*Gardenia jasminoides*) fruit from which pigment is removed.

The present invention further provides a quasi-pharmaceutical product for preventing or alleviating allergic disease comprising, as an active ingredient, an extract of *gardenia* (*Gardenia jasminoides*) fruit from which pigment is removed.

The present invention still further provides a functional health food composition for preventing or alleviating allergic disease comprising, as an active ingredient, an extract of *gardenia* (*Gardenia jasminoides*) fruit from which pigment is removed.

The present invention relates to a composition for preventing, alleviating, or treating allergic skin disease comprising, as an active ingredient, an extract of *gardenia* fruit from which pigment is removed, and since the extract of *gardenia* fruit from which pigment is removed is found to be effective for allergic skin diseases compared to an extract of *gardenia* fruit from which pigment is not removed, the composition can be very advantageously used for allergic skin diseases, in particular, atopic dermatitis.

DETAILED DESCRIPTION

Figure 1:
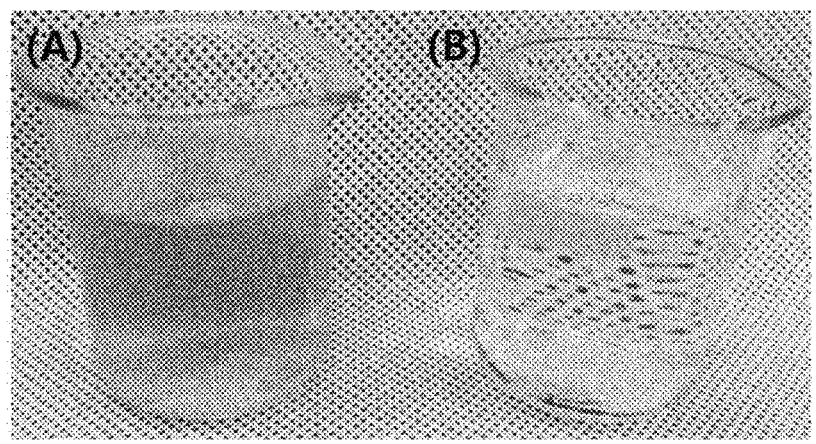
FIG. 1 shows photographic images of (A) an extract of *gardenia* fruit from which pigment is not removed and (B) an extract of *gardenia* fruit from which pigment is removed according to the present invention.

The present invention relates to a pharmaceutical composition for preventing or treating allergic disease comprising, as an active ingredient, an extract of *gardenia* (*Gardenia jasminoides*) fruit from which pigment is removed.

The allergic disease is preferably any one selected from atopic dermatitis, allergic dermatitis, contact dermatitis, skin hives, itch, insect allergy, food allergy, drug allergy, edema, anaphylaxis, allergic rhinitis, asthma, and allergic conjunctivitis, but it is not limited thereto.

The pigment is preferably crocin, but it is not particularly limited as long as it is a pigment contained in an extract of *gardenia* fruit.

The extract of *gardenia* fruit from which pigment is removed as described in the present invention is preferably produced by a method including the followings, but it is not limited thereto:

(1) carrying out first extraction by adding an extraction solvent to *gardenia* fruit followed by filtration to obtain a first filtrate;

(2) adding an extraction solvent to residues remained after obtaining the first filtrate in above step (1) to obtain a second filtrate:

(3) mixing the first filtrate with the second filtrate, which are obtained from the above step (1) and step (2), respectively, followed by adding activated carbon for allowing pigments of *gardenia* fruit extract to get adsorbed onto the activated carbon; and (4) removing the activated carbon after the above step (3) followed by filtration, concentration, and drying to obtain an extract of *gardenia* fruit from which pigment is removed.

The activated carbon in the above step (3) is, although not particularly limited, preferably a granule type or a fine granule type. More preferably, it is a fine granule type (i.e., fine granule or powder form).

The extraction solvent is preferably water, $C_1$-$C_4$ lower alcohol, or a mixture thereof, and more preferably water or ethanol, but it is not limited thereto.

The pharmaceutical composition of the present invention may further comprise a pharmaceutically acceptable carrier, vehicle, or diluent. The pharmaceutically acceptable carrier to be comprised in the pharmaceutical composition of the present invention is those generally used for preparing a formulation, and examples thereof include physiological saline, sterile water, ringer's solution, buffered physiological saline, dextrose solution, maltodextrin solution, glycerol, ethanol, lactose, dextrose, sucrose, sorbitol, mannitol, starch, acacia gum, calcium phosphate, alginate, gelatin, calcium silicate, microcrystalline cellulose, polyvinyl pyrrolidone, cellulose, syrup, methyl cellulose, methylhydroxy benzoate, propylhydroxy benzoate, talc, magnesium stearate, mineral oil, or the like, but it is not limited thereto. Furthermore, in addition to those components, an antioxidant, a buffer solution, a bacteriostatic agent, a diluent, a surfactant, a binding agent, a lubricating agent, a wetting agent, a sweetening agent, a flavoring agent, an emulsifying agent, a suspending agent, a preservative, or the like may be also comprised. The pharmaceutical composition of the present invention may be administered either orally or parenterally, and, in case of parenteral administration, the administration can be made by injection or application on skin. In case of the application on skin, it is preferable to use the composition prepared in a formulation of an ointment, a patch, or a spraying agent. The suitable dosage of the pharmaceutical composition of the present invention may be differently set depending on various factors including formulation method, administration method, age, bodyweight, sex, severeness of disorder, diet of a patient, administration period, administration pathway, excretion rate, and sensitivity of response.

The present invention furthermore relates to a quasi-pharmaceutical product for preventing or alleviating allergic disease comprising, as an active ingredient, an extract of *gardenia* (*Gardenia jasminoides*) fruit from which pigment is removed.

The quasi-pharmaceutical product is preferably a skin preparation for external use, but it is not limited thereto.

As described herein, the term "quasi-pharmaceutical product" means a product corresponding to any one of a product used for treating, alleviating, handling, or preventing diseases of human or animal, a product having either weak or no direct effect on human body and not an apparatus or a machine and those similar to the product, and a preparation employed for bactericidal, insecticidal, and similar use for preventing infectious diseases, and it includes an article excluding a product other than an apparatus, a machine, or a device among the articles used for the purpose of diagnosis, treatment, alleviation, handling, or prevention of a disease of human or animal, and a product other than an apparatus, a machine, or a device among the articles used for exhibiting a pharmaceutical effect on the structure and function of human or animal. Also in included in the quasi-pharmaceutical product are a skin preparation for external use and a personal hygiene product.

When the extract of *gardenia* fruit from which pigment is removed as described in the present invention is used as an additive of a quasi-pharmaceutical product, the extract can be either directly added or used in combination with other quasi-pharmaceutical product or components of a quasi-pharmaceutical product, and it can be suitably used according to a common method. Mixing amount of the active ingredient can be suitably determined depending on the purpose of use. The skin preparation for external use can be used after preparation in form of an ointment, a lotion, a spray, a patch, a cream, a powder, a suspension, a gel preparation, or a gel. Examples of the personal hygiene product preferably include, although not particularly limited thereto, a soap, a cosmetic, a water tissue, a toilet paper, a shampoo, a skin cream, a facial cream, a toothpaste, a lipstick, a fragrance, a make-up formulation, a foundation, a cheek blush, a mascara, an eye shadow, a sunscreen lotion, a hair care product, an air freshener gel, or a cleaning gel. Other examples of the quasi-pharmaceutical product of the present invention include a sterilizing washing agent, a shower foam, a mouthwash, a water tissue, a liquid soap, a hand wash, a humidifier additive, a mask, an ointment, and a filter filler.

The present invention still further relates to a functional health food composition for preventing or alleviating allergic disease comprising, as an active ingredient, an extract of *gardenia* (*Gardenia jasminoides*) fruit from which pigment is removed.

The composition is preferably produced in any one formulation selected from a powder, a granule, a pill, a tablet, a capsule, a candy, a syrup, and a drink, but it is not limited thereto.

The functional health food composition of the present invention can be prepared by directly adding an extract of *gardenia* fruit from which pigment is removed or mixing with other food or food components, and it can be suitably produced according to a common method. Examples of the food to which the extract of *gardenia* fruit from which pigment is removed can be added include caramel, meat, sausage, bread, chocolate, candies, snacks, biscuits, pizza, ramen, other noodles, gums, dairy products including ice cream, various kinds of soup, beverage, tea, drink, alcohol beverage, and vitamin complex, and all functional health food products in general sense are included therein. Namely, type of the food is not particularly limited. The functional health food composition may further comprise various nutritional supplements, a vitamin, a mineral (i.e., electrolyte), a synthetic and natural flavor, a coloring agent, an enhancing agent (cheese, chocolate, or the like), pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonated drink. In addition, fruit flesh for producing natural fruit juice or vegetable drink can be also comprised. Those components can be used either independently or in combination with each other. Furthermore, the functional health food composition of the present invention may also comprise various flavors or natural carbohydrates as an additional component. Examples of the natural carbohydrates include monosaccharides such as glucose or fructose, disaccharides such as maltose or sucrose, polysaccharides such as dextrin or cyclodextrin, and sugar alcohols such as xylitol, sorbitol, or erythritol. Ratio of the natural carbohydrates is, although not particularly important, preferably 0.01 to 0.04 g, and more preferably 0.02 to 0.03 g per 100 g of the composition of the present invention, but it is not limited thereto. As a sweetening agent, a natural sweetening agent such as thaumatin or *stevia* extract and synthetic sweetening agent such as saccharine or aspartame can be used.

Hereinbelow, the present invention is explained in greater detail in view of the Examples. However, the following Examples are given only for specific explanation of the present invention and it would be evident to a person who has common knowledge in the pertinent art that the scope of the present invention is not limited by them.

EXAMPLES

Example 1. Preparation of Extract of *Gardenia* Fruit from which Pigment is Removed In order to solve the problem associated with the pigments of *gardenia* fruit remained in skin, an extract of *gardenia* fruit from which crocin as an intrinsic pigment of *gardenia* fruit is removed was prepared by adsorbing the *gardenia* fruit pigment onto activated carbon.

(1) Preparation of Ethanol Extract of *Gardenia* Fruit from which Pigment is Removed ① Preparation of first extract of *gardenia* fruit: 100 g of *gardenia* fruit were added to 1,000 ml of 70% (v/v) ethanol (i.e., 10× volume), and, according to extraction for 2 hours in a water bath at 55° C. followed by filtration, a first extract was obtained.

② Preparation of second extract of *gardenia* fruit: To the residuals except the above filtrate, 1,000 ml of 70% (v/v) ethanol (i.e., 10× volume) were added again, and, according to extraction at the same conditions as the first extract followed by filtration, a second extract was obtained.

③ Removal of pigments: First of all, two kinds of activated carbon, i.e., activated carbon granule and activated carbon powder, were selected, and then comparison was made between them.

To 150 ml of the 70% (v/v) ethanol extract in which the above first and second extract are present in mixture, 5 g of activated carbon granule or activated carbon powder were added and, by carrying out stirring for 20 hours, pigments were removed. As a result, it was found that content of geniposide, which is an indicator component, is high when activated carbon powder is used. As such, as an extract of *gardenia* fruit from which pigment is removed to be used in the examples of the present invention, the extract of *gardenia* fruit from which pigment is removed by using activated carbon powder was employed.

④ Filtration, concentration, and drying: The extract of *gardenia* fruit from which pigment is removed was filtered, concentrated by centrifuge (at 60° C. or lower), and dried to yield about 25 g of an extract of *gardenia* fruit (FIG. 1).

(2) Preparation of Water Extract of *Gardenia* Fruit from which Pigment is Removed ① Preparation of first extract of *gardenia* fruit: 100 g of *gardenia* fruit were added to 1,000 ml of water (i.e., 10× volume), and, according to extraction for 2 hours in a water bath at 55° C. followed by filtration, a first extract was obtained.

② Preparation of second extract of *gardenia* fruit: To the residuals except the above filtrate, 1,000 ml of water (i.e., 10× volume) were added again, and, according to extraction at the same conditions as the first extract followed by filtration, a second extract was obtained.

③ Removal of pigments: To 150 ml of the water extract in which the above first and second extract are present in mixture, 5 g of activated carbon powder were added, and, by carrying out stirring for 20 hours, pigments were removed.

④ Filtration, concentration, and drying: The water extract of *gardenia* fruit from which pigment is removed was filtered, concentrated by centrifuge (at 60° C. or lower), and dried to yield water extract of *gardenia* fruit.

Thereafter, efficacy for allergic atopic dermatitis was examined using the extracts of *gardenia* fruit from which pigment is removed, which have been obtained in Example 1. As a comparative example, an extract of *gardenia* fruit from which pigment is not removed was used.

Example 2. Determination of Effect on Atopic Dermatitis in Animal Model with Allergic Atopic Dermatitis which has been Applied with Ethanol Extract of *Gardenia* Fruit from which Pigment is Removed On the skin of a 8-week old NC/Nga mouse, 100 mg of an ointment (AD Biostir, Japan) which contains components originating from house dust mite as an antigen causing allergic atopy were applied, total 6 times for 21 days with an interval of 3 to 4 days to induce allergic atopic dermatitis. Seven days after inducing allergic atopic dermatitis, the animal was applied with 1 mg/ml of the pharmaceutical (extract of *gardenia* fruit (GJE 1%), extract of *gardenia* fruit from which pigment is removed (GJE-CR 1%), or tacrolimus), once a day for 14 days.

Thereafter, using the mouse with induced allergic dermatitis, number of itching for 20 minutes and level of skin damage on ear and back of the animal were examined once a week. All the measurement results are expressed in terms of mean and standard deviation (SD), and a difference among test groups was subjected to a statistical analysis using one-way ANOVA. Statistical significance was recognized when p is less than 0.05 ($p<0.05$).

Figure 2:
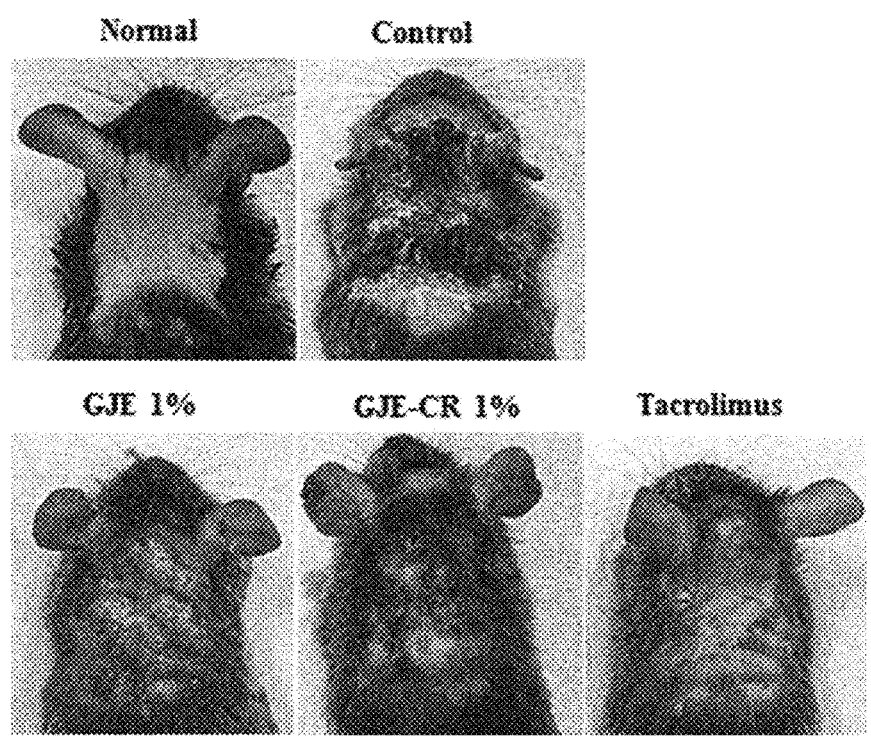
FIG. 2 shows the result of visual examination of the normal group (Normal), control group (Control), group administered with an extract of *gardenia* fruit (GJE 1%), group administered with an extract of de-pigmented *gardenia* (GJE-CR 1%), and positive control group (tacrolimus) using an animal model with allergic atopic dermatitis.
Figure 3:
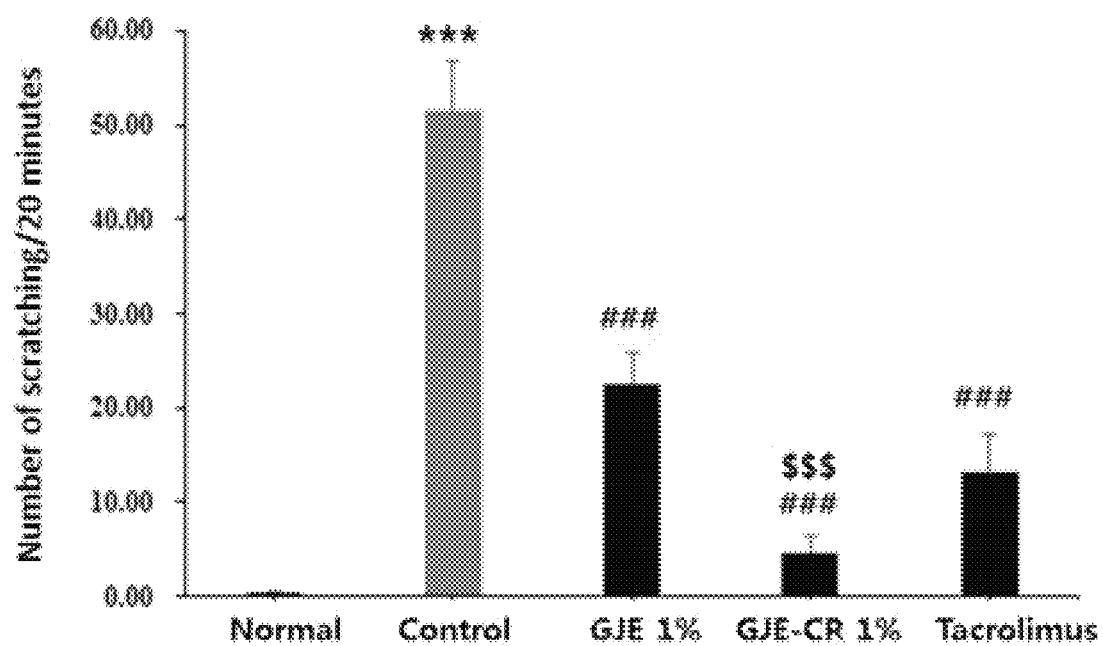
FIG. 3 shows the number of scratching (number of itching) in the normal group (Normal), control group (Control), group administered with an extract of *gardenia* fruit (GJE 1%), group administered with an extract of de-pigmented *gardenia* (GJE-CR 1%), and positive control group (tacrolimus) using an animal model with allergic atopic dermatitis. *** indicates that, compared to the normal group (Normal), the number of scratching has increased with statistical significance in the control group (Control) ($p<0.001$). ###indicates that, compared to the control group (Control), the number of scratching has decreased with statistical significance in the group administered with an extract of *gardenia* fruit (GJE 1%), group administered with an extract of de-pigmented *gardenia* (GJE-CR 1%), and positive control group (tacrolimus) ($p<0.001$). $$$ indicates that, compared to the group administered with an extract of *gardenia* fruit (GJE 1%), the group administered with an extract of de-pigmented *gardenia* of the present invention (GJE-CR 1%) has reduced number of scratching with statistical significance ($p<0.001$).

As the result is shown in FIG. 2, it was found that the skin state of a mouse with induced allergic dermatitis is greatly improved when the animal was treated with an ethanol extract of *gardenia* fruit from which pigment is removed as described in the present invention. It was also found that the number of scratching (i.e., number of itching) is significantly lower than the control group (Control) with induced allergic atopic dermatitis and the number is also lower with statistical significance than the extract of *gardenia* fruit from which pigment is not removed (FIG. 3).

Example 3. Analysis of Change in Inflammatory Cells in Animal Model with Allergic Atopic Dermatitis which has been Applied with Ethanol Extract of *Gardenia* Fruit from which Pigment is Removed Skin tissues of the ear and back of a mouse with induced allergic dermatitis were collected and, by H&E (hematoxylin and eosin) staining and use of an image measuring program (Solution FL ver 9.1), a change in inflammatory cell infiltration was determined. All the measurement results are expressed in terms of mean and standard deviation (SD), and a difference among test groups was subjected to a statistical analysis using one-way ANOVA. Statistical significance was recognized when p is less than 0.05 ($p<0.05$).

Figure 4:
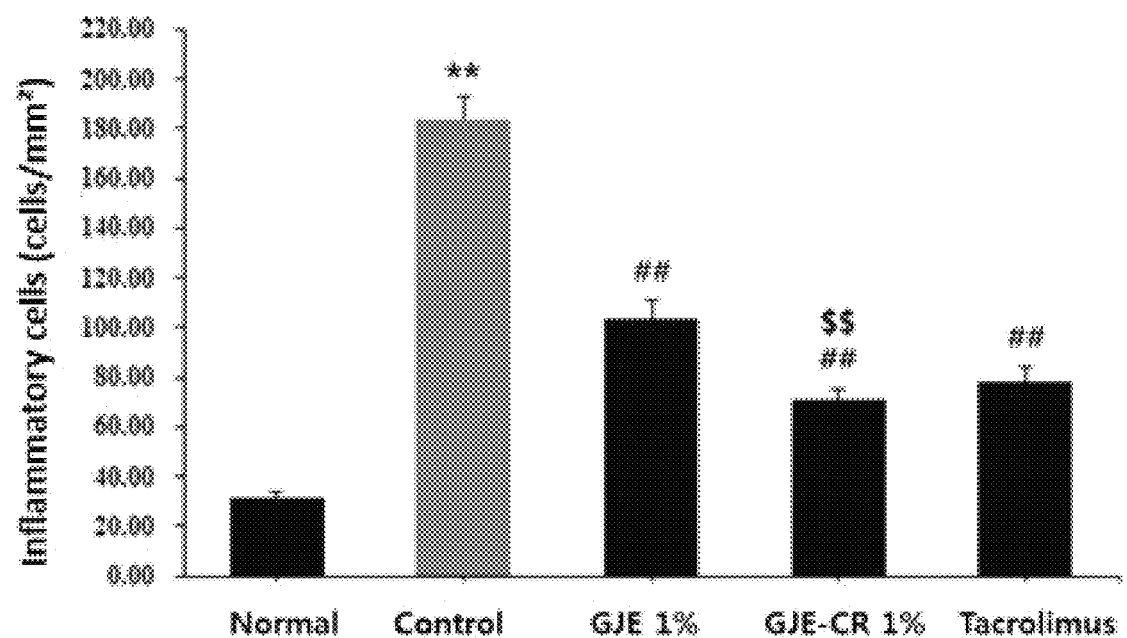
FIG. 4 shows the result of determining inflammatory cells of the normal group (Normal), control group (Control), group administered with an extract of *gardenia* fruit (GJE 1%), group administered with an extract of de-pigmented *gardenia* (GJE-CR 1%), and positive control group (tacrolimus) using an animal model with allergic atopic dermatitis, in which the results are obtained from (A) back or (B) ear of the animal. ** indicates that, compared to the normal group (Normal), the inflammatory cells have increased with statistical significance in the control group (Control) ($p<0.01$). ##and ###indicate that, compared to the control group (Control), the inflammatory cells have decreased with statistical significance in the group administered with an extract of *gardenia* fruit (GJE 1%), group administered with an extract of de-pigmented *gardenia* (GJE-CR 1%), and positive control group (tacrolimus) (##: $p<0.01$, and ###: $p<0.001$). $ and $$ indicate that, compared to the group administered with an extract of *gardenia* fruit (GJE 1%), the group administered with an extract of de-pigmented *gardenia* of the present invention (GJE-CR 1%) has reduced inflammatory cells with statistical significance (##: $p<0.01$, and ###: $p<0.001$).
Figure 4:
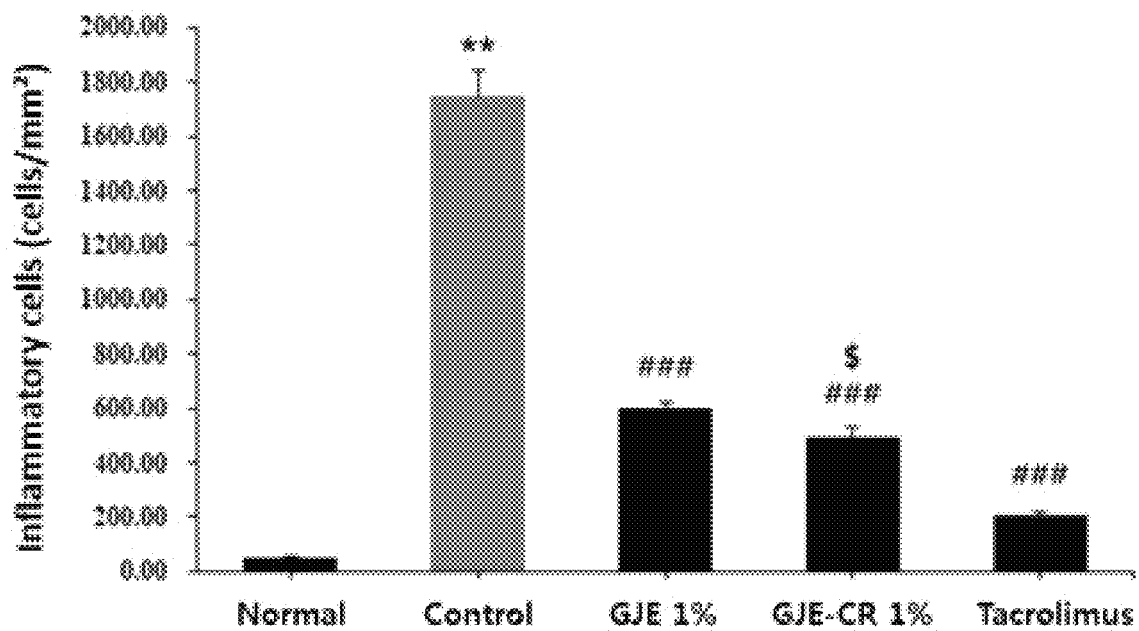

As the result is shown in FIG. 4, it was found that number of inflammatory cells, which is measured for the skin tissues of ear and back of an animal treated with an ethanol extract of *gardenia* fruit from which pigment is removed as described in the present invention, is lower with statistical significance than the number of inflammatory cells from the group with allergic atopic dermatitis (Control). In particular, the lower number of inflammatory cells was shown with statistical difference even when compared to the extract of *gardenia* fruit from which pigment is not removed.

Example 4. Analysis of Number of Mast Cells in Animal Model with Allergic Atopic Dermatitis which has been Applied with Ethanol Extract of *Gardenia* Fruit from which Pigment is Removed Skin tissues of the ear and back of a mouse with induced allergic dermatitis were collected and, by toluidine blue (TB) staining and use of an image measuring program (Solution FL ver 9.1), number of mast cells was determined. All the measurement results are expressed in terms of mean and standard deviation (SD), and a difference among test groups was subjected to a statistical analysis using one-way ANOVA. Statistical significance was recognized when p is less than 0.05 ($p<0.05$).

Figure 5:
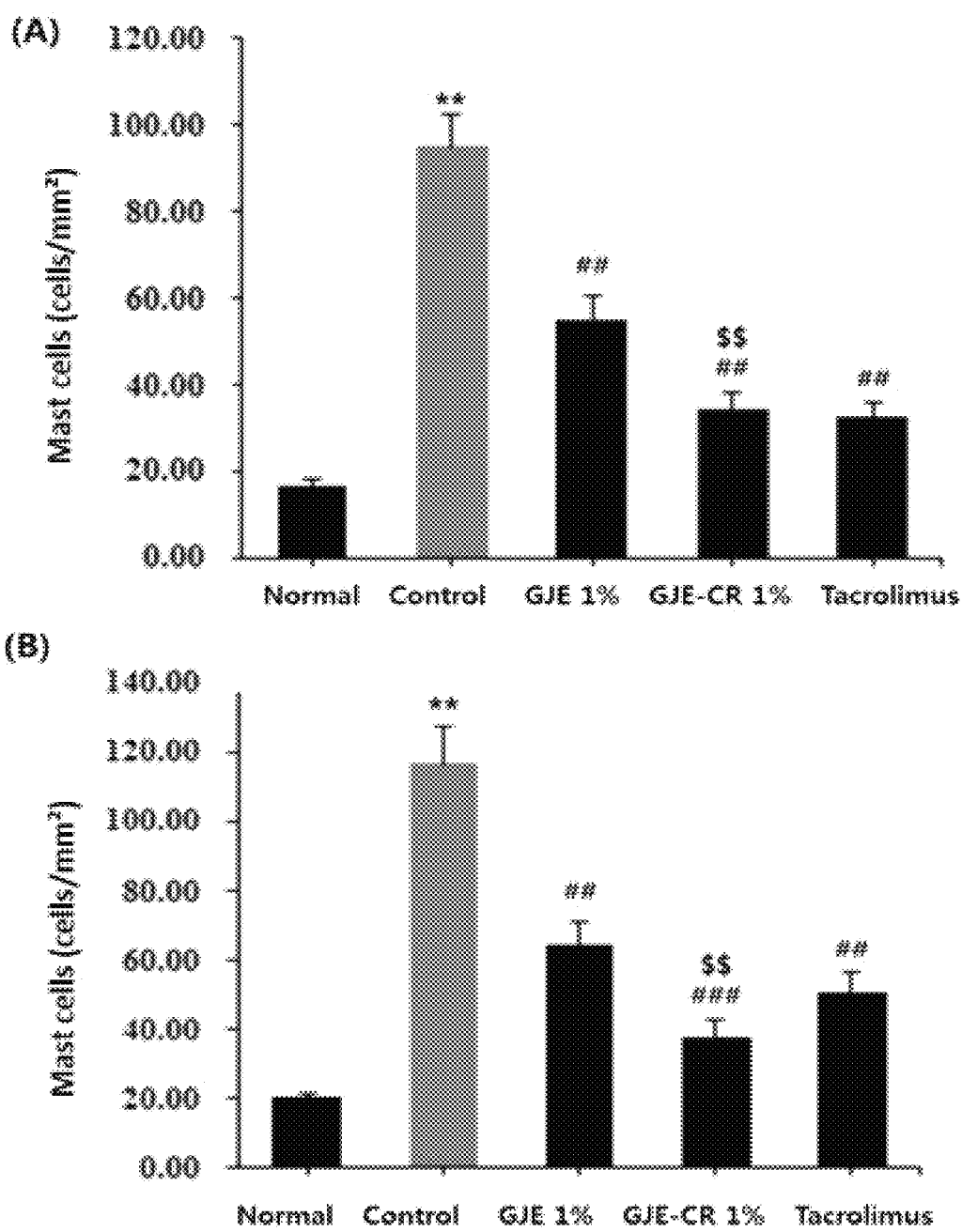
FIG. 5 shows the result of determining mast cells of the normal group (Normal), control group (Control), group administered with an extract of *gardenia* fruit (GJE 1%), group administered with an extract of de-pigmented *gardenia* (GJE-CR 1%), and positive control group (tacrolimus) using an animal model with allergic atopic dermatitis, in which the results are obtained from (A) back or (B) ear of the animal. ** indicates that, compared to the normal group (Normal), the mast cells have increased with statistical significance in the control group (Control) ($p<0.01$). ##and ###indicate that, compared to the control group (Control), the mast cells have decreased with statistical significance in the group administered with an extract of *gardenia* fruit (GJE 1%), group administered with an extract of de-pigmented *gardenia* (GJE-CR 1%), and positive control group (tacrolimus) (##: $p<0.01$, and ###: $p<0.001$). $$ indicates that, compared to the group administered with an extract of *gardenia* fruit (GJE 1%), the group administered with an extract of de-pigmented *gardenia* of the present invention (GJE-CR 1%) has reduced mast cells with statistical significance ($p<0.01$).

As the result is shown in FIG. 5, it was found that number of mast cells, which is measured for the skin tissues of ear and back of an animal treated with an extract of *gardenia* fruit from which pigment is removed as described in the present invention, is lower with statistical significance than the number of mast cells from the animal model group with allergic atopic dermatitis. In particular, the lower number of mast cells was shown with statistical difference even when compared to the extract of *gardenia* fruit from which pigment is not removed.

Example 5. Determination of Number of Itching in Animal Model with Allergic Atopic Dermatitis which has been Orally Administered with Water Extract of *Gardenia* Fruit from which Pigment is Removed On the skin of a 8-week old NC/Nga mouse, 100 mg of an ointment (AD Biostir, Japan) which contains components originating from house dust mite as an antigen causing allergic atopy were applied, total 6 times for 21 days with an interval of 3 to 4 days to induce allergic atopic dermatitis. On a day of starting the test, 150µl of 4% SDS were applied to the animal, and, after allowing it to stand for 1 hour, 100 mg of the house dust mite antigen were applied to back and both ears of the animal, respectively. Seven days after inducing allergic atopic dermatitis, the animal was orally administered with 100 mg/kg or 200 mg/kg of the pharmaceutical (extract of *gardenia* fruit or extract of *gardenia* fruit from which pigment is removed), once a day for 14 days.

Figure 6:
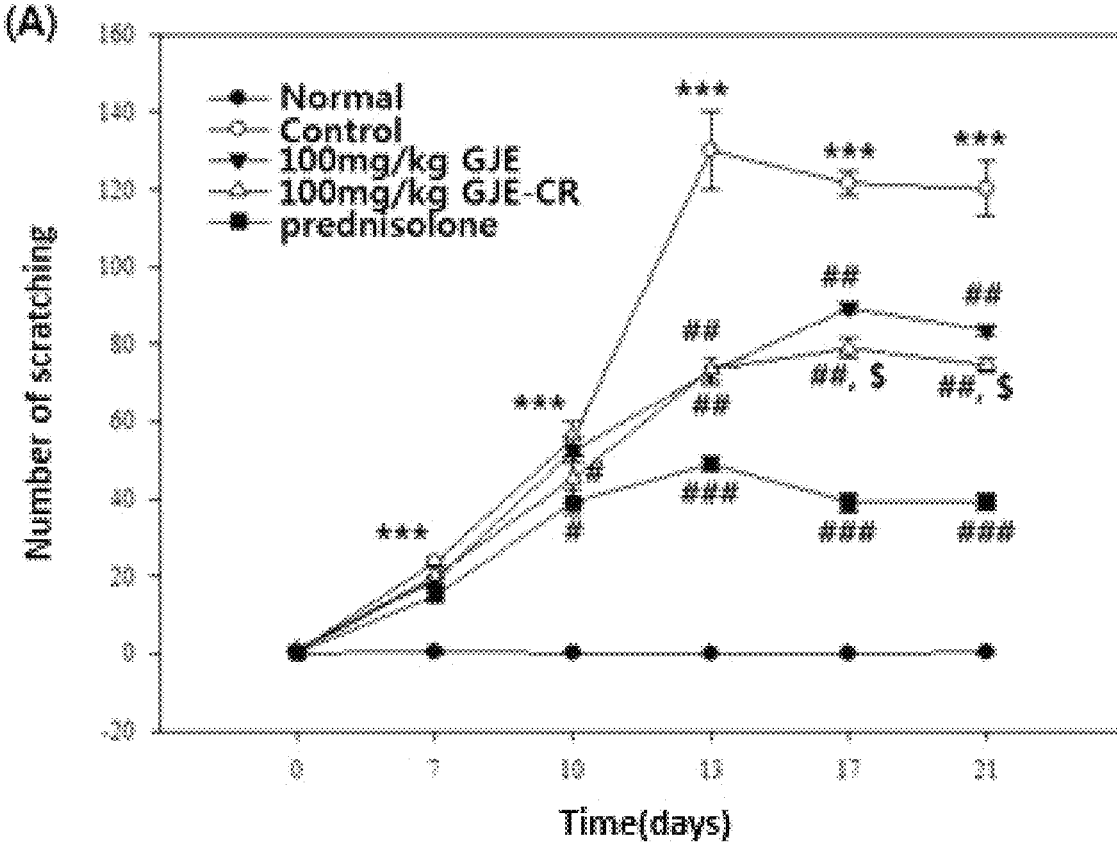
FIG. 6 shows the number of scratching (number of itching) over days in the normal group (Normal), control group (Control), group administered with an extract of *gardenia* fruit (GJE), group administered with an extract of de-pigmented *gardenia* (GJE-CR), and positive control group (prednisolone) using an animal model with allergic atopic dermatitis, in which (A) is the result obtained after administering the pharmaceutical in an amount of 100 mg/kg and (B) is the result obtained after administering the pharmaceutical in an amount of 200 mg/kg. ** indicates that, compared to the normal group (Normal), the number of scratching has increased with statistical significance in the control group (Control) ($p<0.001$). #, ##, and ###indicate that, compared to the control group (Control), the number of scratching has decreased with statistical significance in the group administered with an extract of *gardenia* fruit, group administered with an extract of de-pigmented *gardenia*, and prednisolone group (#: $p<0.05$, ##; $p<0.01$, and ###: $p<0.001$). $ indicates that, compared to the group administered with an extract of *gardenia* fruit (GJE), the group administered with an extract of de-pigmented *gardenia* of the present invention (GJE-CR) has reduced number of scratching with statistical significance ($p<0.05$).
Figure 6:
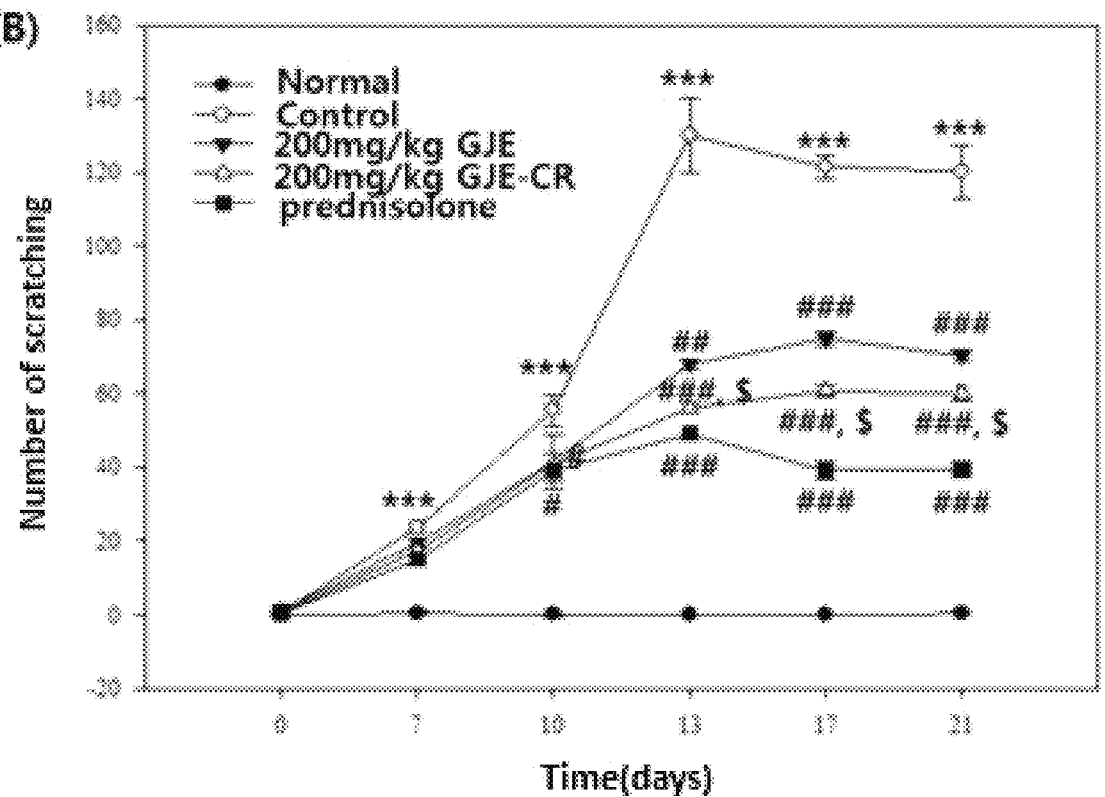

Thereafter, using the animal model with induced allergic dermatitis, number of itching in the ear and back of the animal for 20 minutes was examined once a week to compare the effects obtained according to administration of a pharmaceutical. All the measurement results are expressed in terms of mean and standard deviation (SD), and a difference among test groups was subjected to a statistical analysis using one-way ANOVA. Statistical significance was recognized when p is less than 0.05 ($p<0.05$). As the result is shown in FIG. 6, it was found that, from seven days after inducing allergic dermatitis, number of scratching has increased with statistical significance in the mouse with induced allergic dermatitis compared to the normal group. However, number of scratching has decreased with statistical significance in the group orally administered with an extract of *gardenia* fruit, an extract of *gardenia* fruit from which pigment is removed, or the positive control compared to the group with induced allergic dermatitis (Control). In particular, in case of administering the water extract of *gardenia* fruit from which pigment is removed as described in the present invention, it was shown that the number of scratching has decreased with statistical significance compared to the case of administering the extract of *gardenia* fruit.

What is claimed is:

1. A method for treating an allergic disease, the method comprising administering to a subject in need thereof a composition comprising, as an active ingredient, an extract of *gardenia* fruit from which pigment is removed,
    wherein the pigment is crocin.
2. The method of claim 1, wherein the allergic disease is selected from the group consisting of atopic dermatitis, allergic dermatitis, contact dermatitis, skin hives, itch, insect allergy, food allergy, drug allergy, edema, anaphylaxis, allergic rhinitis, asthma, allergic conjunctivitis, and a combination thereof.
3. The method of claim 1, wherein the extract of *gardenia* fruit from which pigment is removed is produced by:
    carrying out first extraction by adding an extraction solvent to *gardenia* fruit followed by filtration to obtain a first filtrate;
    adding an extraction solvent to residues remained after obtaining the first filtrate to obtain a second filtrate;
    mixing the first filtrate with the second filtrate;
    adding activated carbon for allowing pigment of *gardenia* fruit extract to get adsorbed onto the activated carbon;
    removing the activated carbon; and
    obtaining the extract of *gardenia* fruit from which the pigment is removed by filtration, concentration, and drying.
4. The method of claim 1, wherein the composition is a pharmaceutical composition.
5. The method of claim 1, wherein the composition is included in a quasi-pharmaceutical product.
6. The method of claim 5, wherein the quasi-pharmaceutical product is a skin preparation for external use.
7. The method of claim 1, wherein the composition is a functional health food composition.

* * * * *